United States Patent
Lee et al.

(10) Patent No.: US 10,897,890 B2
(45) Date of Patent: Jan. 26, 2021

(54) MICROCHIP MIMICKING FEMALE REPRODUCTIVE ORGANS AND METHOD FOR FABRICATING THE SAME

(71) Applicant: KANGWON NATIONAL UNIVERSITY University-Industry Cooperation Foundation, Chuncheon-si (KR)

(72) Inventors: Seung Tae Lee, Chuncheon-si (KR); Jung Im Yun, Chuncheon-si (KR); Song Baek, Seoul (KR)

(73) Assignee: Kangwon National University University-Industry Cooperation Foundation, Chuncheon-si (KR)

( * ) Notice: Subject to any disclaimer, the term of this patent is extended or adjusted under 35 U.S.C. 154(b) by 306 days.

(21) Appl. No.: 16/014,138

(22) Filed: Jun. 21, 2018

(65) Prior Publication Data

US 2019/0133109 A1 May 9, 2019

(30) Foreign Application Priority Data

Nov. 3, 2017 (KR) .................. 10-2017-0145678

(51) Int. Cl.
| | |
|---|---|
| *A01N 1/02* | (2006.01) |
| *C12N 5/071* | (2010.01) |
| *C12M 3/06* | (2006.01) |
| *G01N 1/30* | (2006.01) |
| *C12M 1/22* | (2006.01) |
| *C12N 5/075* | (2010.01) |
| *A61D 19/02* | (2006.01) |
| *C12N 5/076* | (2010.01) |
| *C12M 1/32* | (2006.01) |

(52) U.S. Cl.
CPC ............... *A01N 1/02* (2013.01); *C12M 23/16* (2013.01); *C12N 5/0612* (2013.01); *A61D 19/02* (2013.01); *C12M 23/10* (2013.01); *C12M 23/12* (2013.01); *C12N 5/061* (2013.01); *C12N 5/0609* (2013.01); *G01N 1/30* (2013.01)

(58) Field of Classification Search
CPC ....... A01N 1/02; C12M 23/16; C12N 5/0612; C12N 5/061
USPC ........................................................ 600/33
See application file for complete search history.

(56) References Cited

PUBLICATIONS

Lin Xie et al, Integration of Sperm Motility and Chemotaxis Screening with a MicroChannel-Based Device, 2010, Clinical Chemistry 56:8, 1270-1278 (Year: 2010).*

Xiao-Dong Zhang et al., "The effects of different sperm preparation methods and incubation time on the sperm DNA fragmentation", Human Fertility, 2011, pp. 187-191, vol. 14, No. 3.

* cited by examiner

*Primary Examiner* — John P Lacyk
(74) *Attorney, Agent, or Firm* — Rabin & Berdo, P.C.

(57) ABSTRACT

A microchip includes a first chamber and second chamber formed to a predetermined depth in a member made of polydimethylsiloxane (PDMS); and a channel (microchannel) connecting the first chamber to the second chamber. These components mimic in vivo organs which produce by selecting capacitated motile sperm from semen and causing the selected sperm to meet mature oocyte, and these components are capable of effectively producing motile capacitated good-quality sperms from sperms ejaculated outside the body.

2 Claims, 6 Drawing Sheets

MICROCHIP MIMICKING FEMALE REPRODUCTIVE ORGANS AND METHOD FOR FABRICATING THE SAME

BACKGROUND OF THE INVENTION

Field of the Invention

The present invention relates to a microchip that mimics female reproductive organs, and more particularly to a microchip which is capable of effectively producing capacitated motile good-quality sperms from sperms ejaculated outside the body, by mimicking in vivo organs which produce embryos by selecting capacitated motile sperms from semen and causing the selected sperms to meet mature oocytes.

Description of the Prior Art

Excessively low birth-rate has become a problem not only in Korea but also in the world, and the incidence of infertility is increasing rapidly due to decreased fertility of advanced age women, increased genital disease, increased stress and environmental pollution, and the like. Thus, in order to overcome this infertility or sterility, various assisted reproductive technologies such as ovulation induction, intrauterine insemination (IUI), in vitro fertilization (IVF), embryo transfer (ET), intra-cytoplasmic sperm injection (ICSI) and the like have been developed and applied in actual clinical practice. In particular, among these various assisted reproductive technologies, embryo transfer (ET) of in vitro fertilized embryos produced by in vitro fertilization (IVF) has been most frequently applied in clinical practice in Korea and abroad.

In the production of in vitro fertilized embryos by in vitro fertilization, the production of good-quality in vitro fertilized embryos is an important factor for successful pregnancy. In addition, in the production of in vitro fertilized embryos by in vitro fertilization, a process of efficiently selecting motile sperm is also very important.

To this end, a variety of in vitro sperm processing techniques, including the swim-up method, have been developed and used. However, in these techniques, long-term in vitro exposure of sperm, and thus increased damage to sperm DNA is then induced [Zhang et al., 2011]. Therefore, the integrity of sperm DNA together with the motility of sperm is important in the production of good-quality blastocysts through production of good-quality in vitro fertilized embryos and is also very important for the successful birth of a normal child from such a good-quality blastocyst.

Conventionally, the production of in vitro fertilized embryos by in vitro fertilization has been performed by retrieving fertilizable mature sperm from semen and artificially causing the sperms to meet mature oocytes in vitro. In order to select capacitated sperms from sperms present in semen, two steps, that is, a step of selecting motile sperms and a step of enabling these sperms to have fertilization ability, should be performed. In addition, in order to produce in vitro fertilized embryos, a step of co-culturing selected motile sperms having fertilization ability with mature oocytes should be performed.

Each of the steps shows a tendency to be highly dependent on the superiority of an assisted reproductive technology system established for each organ and the ability of the practitioner. In addition, during selection of capacitated motile sperms, the possibility of contamination with abnormal sperms is very high. For this reason, these abnormal sperms are highly likely to meet mature oocytes during in vitro fertilization, making it difficult to produce good-quality in vitro fertilized embryos.

PRIOR ART DOCUMENTS

Non-Patent Documents (Non-Patent Document 0001) Zhang X D, Chen M Y, Gao Y, Han W, Liu D Y, Huang G N (2011): The effects of different sperm preparation methods and incubation time on the sperm DNA fragmentation. Hum Fertil 14(3):187-191.

SUMMARY OF THE INVENTION

To solve infertility problems based on improvement in the efficiency of assisted reproductive technologies, it is very important to produce good-quality in vitro fertilized embryos. This fundamentally requires a technology capable of easily selecting good-quality capacitated motile sperms from semen and a technology capable of effectively producing embryos by causing these sperms to meet mature oocytes.

Therefore, it is an object of the present invention to provide a microchip which is capable of easily selecting good-quality capacitated motile sperms from semen, by structurally mimicking in vivo organs, including vagina, cervix, uterus, isthmus, and fallopian tube, which produce embryos by selecting capacitated motile sperms from semen and causing the selected sperms to meet mature oocytes.

However, objects which are to be achieved by the present invention are not limited to the above-mentioned objects, and other objects of the present invention will be clearly understood by those skilled in the art from the following description.

A first aspect of the present invention is directed to a microchip mimicking female reproductive organs, the microchip including: a first chamber formed in in a predetermined member and having a predetermined depth; a second chamber formed in the member and having a predetermined depth; and a channel connected to the bottom of each of the first chamber and the second chamber and connecting the first chamber to the second chamber.

A second aspect of the present invention is directed to a method for fabricating a microchip mimicking female reproductive organs, the method including the steps of: mixing liquid polydimethylsiloxane with a curing agent, thereby preparing a mixture solution; removing bubbles from the mixture solution; and pouring the mixture solution, from which the bubbles have been removed, into a mold, and curing the poured mixture solution.

In the method, the mold is a mold for forming a first chamber and a second chamber to a predetermined depth, and a channel connected to the bottom of each of the first chamber and the second chamber and connecting the first chamber to the second chamber.

A third aspect of the present invention is directed to a method for producing capacitated motile sperms, the method including the steps of: injecting sperms into the first chamber of the microchip mimicking female reproductive organs; incubating the microchip for a predetermined time; and selecting sperms that moved to the second chamber through the channel.

The above-described technical solutions are only illustrative and are not intended to limit the scope of the present invention. In addition to the above-described exemplary embodiments, additional embodiments and examples as described in the following detailed description may be contemplated.

DETAILED DESCRIPTION OF THE INVENTION

Figure 1:
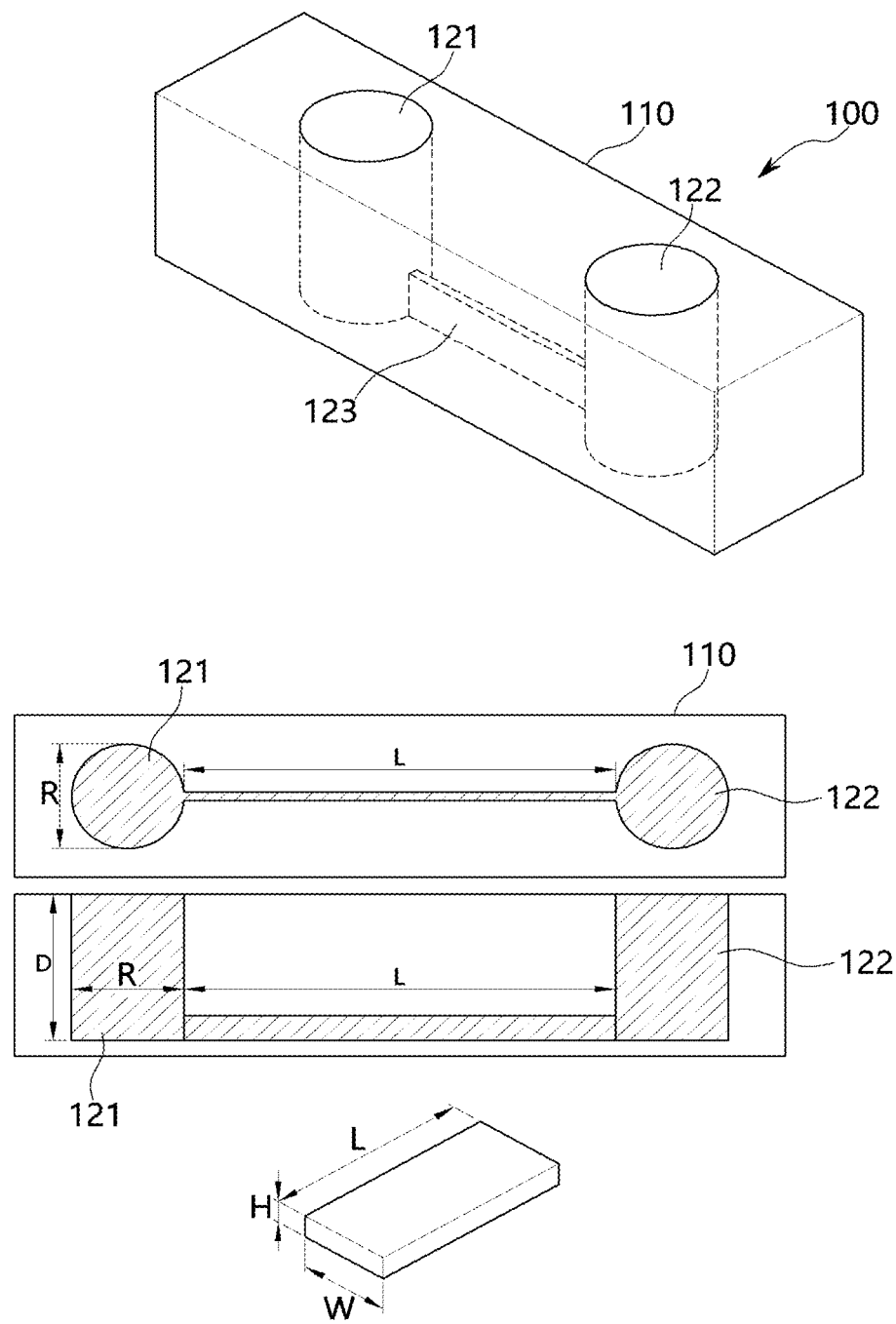
FIG. 1 shows an example of a microchip according to the present invention.

Hereinafter, embodiments of the present invention will be described in detail with reference to the accompanying drawings so that they can be readily implemented by those skilled in the art. However, the present invention may be embodied in a variety of different forms and should not be construed as limited to the embodiments set forth herein. In the drawings, parts unrelated to the description are omitted in order to clearly explain the present invention.

Throughout the specification, when any part is referred to as "including" any component, it does not exclude other components, but may further include other components, unless otherwise specified.

Through the specification, words of degree, such as "about", "substantially", and the like are used herein in the sense of "at, or nearly at, when given the manufacturing and material tolerances inherent in the stated circumstances" and are used to prevent the unscrupulous infringer from unfairly taking advantage of the invention disclosure where exact or absolute figures are stated as an aid to understanding the invention.

Although terms such as first, second and the like may be used to describe various components, but these components should not be limited by these terms. These terms are used only for the purpose of distinguishing one component from other components.

Hereinafter, a microchip mimicking female reproductive organs, a fabrication method thereof, and a method for producing capacitated motile sperm will be described in detail with reference to exemplary embodiments, examples and the accompanying drawings. However, the scope of the present invention is not limited to these exemplary embodiments, examples and drawings.

FIG. 1 shows one embodiment of a microchip 100 mimicking female reproductive organs according to the present invention. As can be seen therein, the microchip 100 includes: a first chamber 121 in a predetermined member and having a predetermined depth; a second chamber formed in the member and having a predetermined depth; and a channel connected to the bottom of each of the first chamber 121 and the second chamber 122 and connecting the first chamber 121 to the second chamber 122.

Each of the first chamber 121 and the second chamber 122 refers to a space formed to have a predetermined size and shape, and the channel 123 is configured to connect the first chamber 121 to the second chamber 122 and serves as a pathway through which sperms move.

The member 110, in which the first chamber 121, the second chamber 122 and the channel 123 are formed, may be made of various materials having various properties. Preferably, the member 110 may include polydimethylsiloxane (PDMS).

The first chamber 121 and the second chamber 122 may have various sizes or shapes.

In a specific embodiment, the first chamber 121 and the second chamber 122 may have a cylindrical shape, but are not limited thereto.

When the first chamber 121 and the second chamber 122 have a cylindrical shape, the diameter (R) of each of the first 121 and the second chamber 122 may be about 0.5 cm, but is not limited thereto. For example, the diameter of each of the first 121 and the second chamber 122 may be 0.4 cm to 0.6 cm.

In addition, the depth (D) of each of the first chamber 121 and the second chamber 122 may be about 0.75 cm, but is not limited thereto.

The channel 123 that connects the first chamber 121 to the second chamber 122 may have various sizes and shapes. In a specific embodiment, the channel 123 that connects the first chamber 121 to the second chamber 122 may have a straight line shape, but is not limited thereto.

In addition, the channel 123 that connects the first chamber 121 to the second chamber 122 may have a rectangular tube shape, but is not limited thereto.

When the channel 123 that connects the first chamber 121 to the second chamber 122 has a rectangular tube shape, the length (L) of the channel 123, that is, the length from a point at which the channel 123 is connected to the first chamber to a point at which the channel 123 is connected to the second chamber 122, may vary. In a specific embodiment, the length (L) of the channel 123 may be about 1.5 cm, but is not limited thereto. For example, the length (L) of the channel 123 may range from 1.3 cm to 1.7 cm.

The width (W) and height (H) of the channel 123 may vary.

In a specific embodiment, the width (W) of the channel 123 may be about 200 μm, and the height (H) of the channel 123 may be about 60 μm, but are not limited thereto. For example, the width of the channel 123 may range from 175 μm to 225 μm, and the height (H) of the channel 123 may range from 50 μm to 70 μm.

In the microchip 100 according to the present invention, the first chamber 121, the second chamber, and the channel 123 that connects the first chamber 121 to the second chamber 122 may perform functions similar to those of female reproductive organs.

Figure 2:
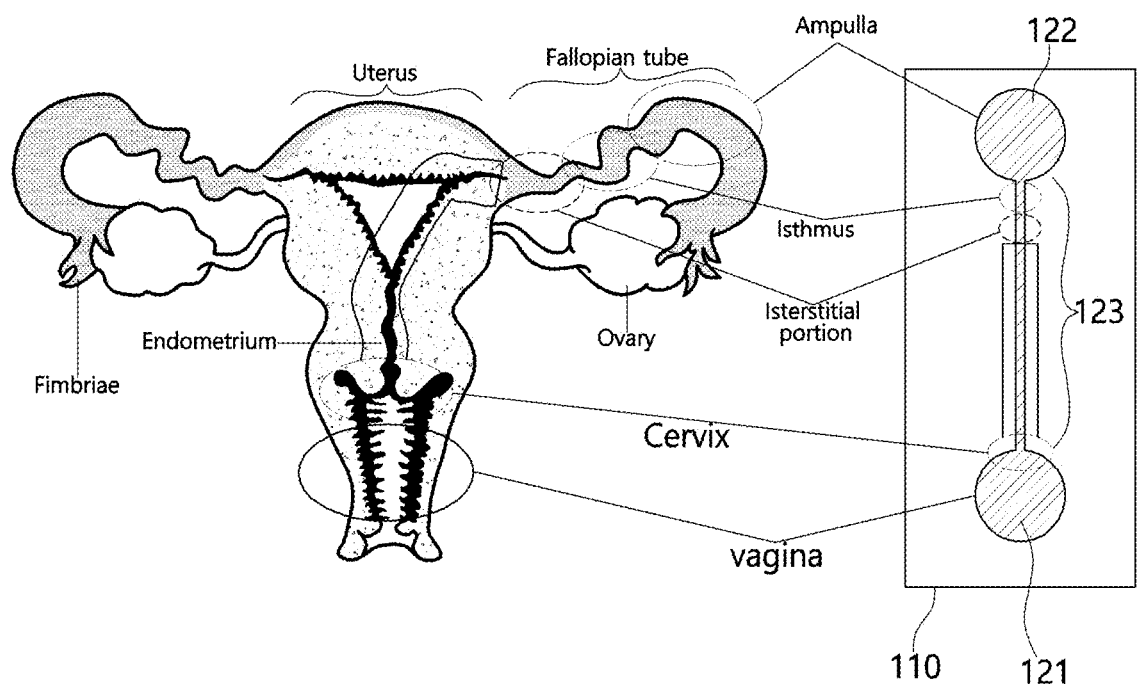
FIG. 2 illustrates that a microchip according to the present invention mimics female reproductive organs.

FIG. 2 shows the correspondence between the components of the microchip 100 according to the present invention and female reproductive organs (including vagina, cervix, uterus, isthmus, and fallopian tube) which are involved in in vivo fertilization processes.

As can be seen therein, the cervix, uterus and isthmus, to which sperms present in the vagina have to move in order to meet oocytes in the fallopian tube, are connected to one another by a single channel, and the vagina and the fallopian tube are connected to each other by this channel. Namely, the vagina and the fallopian tube correspond to the first chamber 121 and the second chamber 122, respectively, and the cervix, uterus and isthmus, through which sperm moves, correspond to a microchannel which is a single elongated channel having a straight line shape.

Figure 3:
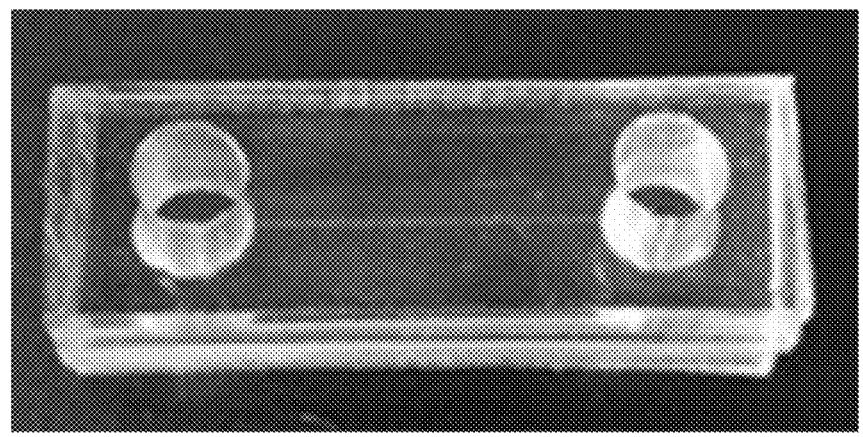
FIG. 3 shows a photograph of an example of a microchip according to the present invention.

FIG. 3 shows a photograph of a microchip 100 mimicking female reproductive organs according to one embodiment of the present invention. Namely, FIG. 3 shows the appearance of the microchip 100 in which the first chamber 121 and the second chamber 122 are formed in a transparent member 110. FIG. 3 is only an example to help understand the present invention, and the present invention can be variously configured as needed.

Hereinafter, a method for fabricating the microchip 100 mimicking female reproductive organs according to one embodiment of the present invention will be described in detail.

First, liquid polydimethylsiloxane (PDMS) and a curing agent are mixed to each other, thereby preparing a mixture solution (S210). In a specific embodiment of step S210, polydimethylsiloxane (PDMS; Dowdoring, Seoul, Korea), a kind of silicone, may be mixed with a curing agent at a ratio of 10:1 (wt/wt), but is not limited thereto.

Then, bubbles are removed from the mixture solution prepared in step S210 (S220).

A method of removing bubbles in step S220 may be performed in various ways. In a specific embodiment, the method may be performed by placing the prepared mixture solution in a container connected to a vacuum pump and applying a vacuum to the mixture solution, thereby removing bubbles therefrom, but is not limited thereto.

Then, the mixture solution from which bubbles have been removed is poured and cured in a mold (S230 and S240).

In a specific embodiment, the PDMS/curing agent mixture solution, from which bubbles have been removed in step S220, is poured into a mold for forming the first chamber 121, the second chamber 122 and the channel 123 which is connected to the bottom of each of the first chamber 121 and the second chamber 122 and which connects the first chamber 121 to the second chamber 122 (S230). In this regard, the mold may be configured such that a plurality of the microchips 100 may be fabricated simultaneously.

Thereafter, the mixture solution in the mold may be cured on a hot plate for a predetermined time (S240). In this respect, the temperature of the hot plate may be set at about 85° C., and the curing time may be about 2 hours and 30 minutes, but are not limited thereto.

In addition, the method for fabricating the microchip 100 mimicking female reproductive organs according to one embodiment of the present invention may further include step S250 of separating the cured material, obtained in step S240, from the mold, forming holes for the first chamber 121 and the second chamber 122, and cutting the cured material to a size to be used in an experiment.

Namely, holes for the first chamber 121 and the second chamber 122, which may be blocked when steps S230 and S240 are performed, may be formed, and the cured material separated from the mold may be cut to a suitable size so that it can be used in an experiment.

In this regard, the mold refers to a mold related to each embodiment of the microchip 100 mimicking female reproductive organs according to the present invention. Namely, it is a mold for forming the first chamber 121, the second chamber 122 and the channel 123 in the PDMS member 110.

The mold may be configured such that the first chamber 121 and the second chamber 122 may be formed to have a cylindrical shape, but is not limited thereto.

The mold may be configured such that the first chamber 121 and the second chamber 122, which have a cylindrical shape, are formed to have a diameter of about 0.5 cm, but is not limited thereto. For example, the mold may be configured such that the first chamber 121 and the second chamber 122, which have a cylindrical shape, are formed to have a diameter ranging from 0.4 cm to 0.6 cm.

The mold may be configured such that the channel 123 connecting the first chamber 121 to the second chamber 122 is formed to have a straight line shape, but is not limited thereto.

The mold may be configured such that the channel 123 connecting the first chamber 121 to the second chamber 122 is formed to have a rectangular tube shape, but is not limited thereto.

When the channel 123 that connects the first chamber 121 to the second chamber 122 is formed to have a rectangular tube shape, the mold may be configured such that the channel 123 is formed to have a length of about 1.5 cm, but is not limited thereto. For example, the mold may be configured such that the channel 123 that connects the first chamber 121 to the second chamber 122 is formed to have a length ranging from 1.3 cm to 1.7 cm.

In addition, the mold may be configured such that the channel 123 is formed to have a width ranging from 175 μm to 225 μm and a height ranging from 50 μm to 70 μm, but is not limited thereto.

A method for producing capacitated motile sperm according to the present invention may include the steps of: injecting sperms into the first chamber 121 of a microchip; incubating the microchip for a predetermined time; and retrieving sperm that moved into the second chamber 122 through the channel 123.

As used herein, the term "microchip" refers to the microchip 100 mimicking female reproductive organs according to each embodiment as described above.

The step of incubating the microchip for a predetermined time may be performed in a 5% $CO_2$ incubator at 37° C. In addition, the incubation time may vary. For example, the incubation time may be 90 minutes, but is not limited thereto. For example, the incubation time may be 80 to 100 minutes.

In the production of in vitro fertilized embryos by in vitro fertilization, the production of good-quality in vitro fertilized embryos is an important factor for successful pregnancy. In addition, in the production of in vitro fertilized embryos by in vitro fertilization, a process of efficiently selecting motile sperm is also very important.

In connection with this, the producing capacitated motile sperm according to the present invention enables motile sperm to be efficiently selected using the microchip 100.

Hereinafter, the present invention will be described in further detail with reference to examples. It is to be understood, however, that these examples are for illustrative purposes only and are not intended to limit the scope of the present invention.

Hereinafter, for convenience of explanation and understanding, the term "channel 123" which is a component of the microchip 100 according to the present invention will be used interchangeably with the term "microchannel".

EXAMPLES

1. Materials and Method

1.1. Animals

In this Example, 9-week-old female ICR mice and 9-week-old male ICR mice were used, which were all purchased from Dae Han Bio Link Co., Ltd. (Korea). All animal experiments performed were approved by the Animal Experiments Ethical Committee of Kangwon National University (No:KW-170117-1).

1.2. Fabrication of Silicone-Based Microchip

Figure 4:
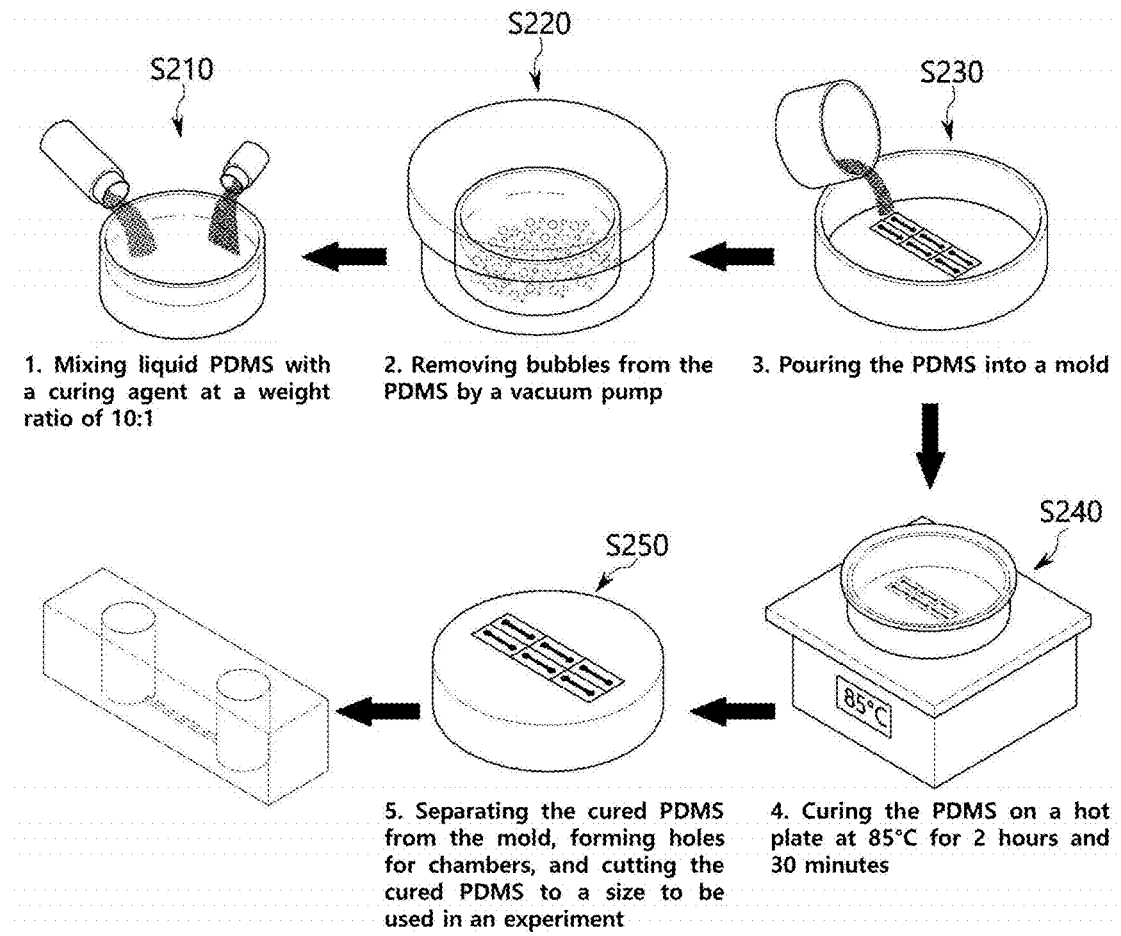
FIG. 4 shows an example of a method for fabricating a microchip according to one embodiment of the present invention.

As shown in FIG. 4, PDMS (polydimethylsiloxane; Dowdoring, Seoul, Korea), a kind of silicone, was mixed with a curing agent at a ratio of 10:1 (wt/wt). The PDMS mixture solution was placed in a container connected to a vacuum pump, and a vacuum was applied thereto, thereby removing bubbles from the PDMS solution. The PDMS solution, from which bubbles have been removed, was filled into each of molds having the dimensions shown in FIGS. 5 to 7, and was cured on a hot plate at 85° C. for 2 hours and 30 minutes. The completely cured PDMS was separated from the molds, sterilized, and then used in each experiment.

1.3. Design of Experiments

In order to optimize the physical conditions of a microchannel through which capacitated motile sperm can efficiently move in a microchip, microchips including microchannels having various widths, heights and lengths were fabricated, and the mobility of capacitated mature sperms in these microchips was examined. Non-capacitated motile sperms were injected into one chamber, and then the number of sperms that moved to the other chamber through the microchannels under capacitation inducing conditions was measured, thereby determining the width, height and height of the microchannel through which the largest number of sperms moved.

Next, in order to examine the efficiency with which the microchip having optimal conditions produces capacitated mature sperm, the survival rate and degree of capacitation of sperms that moved through the microchip were measured.

In addition, in order to examine the efficiency with which in vitro fertilized embryos are produced in the optimized microchip for production of capacitated sperms, mouse cumulus-oocyte cell complexes (COCs) were injected into the chamber in which the produced capacitated sperms were collected, and the in vitro fertilization of the oocytes was measured.

Finally, quality analysis of the in vitro fertilized embryos produced by the microchip was performed by measuring the 2-cell stage embryo, 4-cell stage embryo and blastocyst formation rates through in vitro culture of the produced in vitro fertilized embryos.

In all experiments, the induction of capacitation and in vitro fertilization of ejaculated sperms were performed in 4-well culture dishes, and they were used as a control in each experiment.

1.4. Sperm Retrieval

A 9-week-old male ICR mouse was sacrificed by cervical dislocation, and then the epididymis of the male mouse was dissected and added to PBS containing 0.5% (wt/v) bovine serum albumin (BSA; Sigma-Aldrich, Mo., St. Louis, USA). The epididymis was defatted using forceps on a hot plate at 37° C., and then transferred to fresh PBS. The defatted epididymis was transferred again to a Petri dish containing 2 ml of M16 medium (Sigma-Aldrich), and then the epididymal tail was cut and the epididymis was incubated at 37° C. in a 5% $CO_2$ atmosphere for 20 minutes, thereby retrieving sperms from the epididymis.

1.5. Analysis of Sperm Survival Rate

An Eosin-Nigrosin solution containing 0.5% (wt/v) Eosin Y (Sigma-Aldrich) and 10% (wt/v) Nigrosin (Sigma-Aldrich) was prepared, and sperms were stained with a 1:1 (v/v) mixture of sperm-containing M16 medium and the Eosin-Nigrosin solution.

Then, the stained sperms were applied thinly to slide glass, treated with 99% glycerol, and then covered with cover glass. Next, the percentages of stained sperms (dead sperms) and unstained sperms (living sperms) were measured under a stereomicroscope (SZ61, Olympus, Tokyo, Japan).

1.6. Analysis of Sperm Capacitation and Whether Sperms Would be Capacitated The mature sperms retrieved from the epididymis tail were cultured in M16 medium containing 0.3% (w/v) BSA at 37° C. in a 5% $CO_2$ atmosphere for 90 minutes, thereby inducing capacitation of the mature sperms. Next, the M16 medium containing the capacitation-induced sperms was centrifuge at 1755 rpm for 3 minutes.

After removal of the supernatant, the obtained sperm pellet was washed with PBS, fixed in 4% (v/v) formaldehyde (JUNSEI, Tokyo, Japan) for 20 minutes, and washed again with PBS.

The fixed, capacitation-induced sperms were washed with 1M ammonium acetate (Sigma-Aldrich), applied to slide glass, and dried. Next, the slide glass having the fixed sperms applied thereto was stained in 0.4% (wt/v) Coomassie G-250 (Sigma-Aldrich) solution containing 3.5% (v/v) perchloric acid (Sigma-Aldrich) for 10 minutes, and it was treated with 99% glycerol and then covered with cover glass.

Next, the percentages of stained sperms (dead sperms) and unstained sperms (living sperms) were measured under a stereomicroscope.

1.7. Retrieval of Mature Oocytes

5 IU pregnant mare serum gonadotropin (PMSG; Sigma-Aldrich) was injected intraperitoneally into a 9-week-old female ICR mouse, and after 48 hours, 5 IU human chorionic gonadotropin (hCG; LG Life Sciences) was injected intraperitoneally into the same female mouse. At 16 hours after hCG was injected intraperitoneally into the female mouse, the female mouse was sacrificed by cervical dislocation, and the oviduct was dissected and added to 0.5% (wt/v) BSA-containing PBS pre-warmed to 37° C.

The dissected oviduct was transferred to a Petri dish containing 2 ml of M2 medium (Sigma-Aldrich) on a hot plate at 37° C., and the fallopian tube was cut using forceps, thereby retrieving cumulus-oocyte cell complexes (COCs).

1.8. Production of In Vitro Fertilized Embryos in Conventional Plastic Culture Dish The mature sperms retrieved from the epididymal tail were further cultured in M16 medium containing 0.5% (wt/v) BSA at 37° C. in a 5% $CO_2$ atmosphere for 90 minutes, thereby inducing capacitation of the mature sperms.

Next, the total number of capacitated mature sperms was measured using a blood cell counting chamber. For in vitro fertilization of mature oocytes with capacitated mature sperms, $5 \times 10^5$ capacitated sperms were cultured in M16 medium containing cumulus-oocyte cell complexes at 37° C. in a 5% $CO_2$ atmosphere for 6 hours.

Next, embryos having both a pronucleus and a second polar body were selected under a stereomicroscope (SZ61, Olympus, Tokyo, Japan) and used in in vitro culture.

1.9. Production of In Vitro Fertilized Embryos in Microchip

M16 medium containing 0.3% (w/v) BSA was filled into the microchip and incubated at 37° C. in a 5% $CO_2$ atmosphere for 2 hours.

Next, $5 \times 10^5$ mature sperms obtained from the epididymal tail were injected into one chamber of the microchip, and the cumulus-oocyte cell complexes (COCs) obtained from the mouse oviduct were injected into the other chamber. The sperms and the cumulus-oocyte cell complexes were cultured at 37° C. in a 5% $CO_2$ atmosphere for 6 hours, and then embryos having both the pronucleus and the second polar body were selected under a stereomicroscope and used in in vitro culture.

1.10. In Vitro Culture of In Vitro Fertilized Embryos

The retrieved in vitro fertilized embryos were cultured in M16 medium at 37° C. in a 5% $CO_2$ atmosphere. After 48 hours of culture, the embryos developed to the 4-cell stage were transferred to M16 medium further containing 3 mg/ml BSA. Then, the 4-cell embryos were further cultured for 72 hours without replacing medium.

1.11. Statistical Analysis

All the experimental results obtained in this Example were statistically analyzed using the general linear model (PROC-GLM) in the statistical analysis system (SAS) program, and significance tests for each experiment were performed using the Analysis of Variance (ANOVA) Procedure included in the SAS package. Next, a significant difference between treatment groups was measured using the Least-Square or DUNCAN method. In addition, P value<5% was considered significant between the treatment groups.

2. Results 2.1. Fabrication of Microchip Mimicking Female Reproductive Organs

First, a silicone-based microchip structurally mimicking the vagina, cervix, uterus, isthmus, and fallopian tube, which are absolutely involved in in vitro fertilization processes, was fabricated. As shown in FIG. 1, the cervix, uterus and isthmus, to which sperms present in the vagina have to move in order to meet oocytes in the fallopian tube, were designed to be connected to one another by a single channel, and the vagina and the fallopian tube were configured such that they would be connected to each other by this channel.

For microchip portions corresponding to the vagina and the fallopian tube, circular portions having a diameter of about 0.5 cm were fabricated, and for microchip portions corresponding to the cervix, uterus and isthmus through which sperms move, a microchannel which is a single elongated channel having a straight line shape was fabricated.

In order to optimize the structural conditions of a microchannel through which sperms can easily move to the fallopian tube, microchips including microchannels having various widths, heights and lengths were fabricated, and motile sperms retrieved from the epididymal tail were injected into one chamber of the microchip, and then the percentages of sperms that moved to the opposite chamber through the microchannel was measured.

Figure 5A:
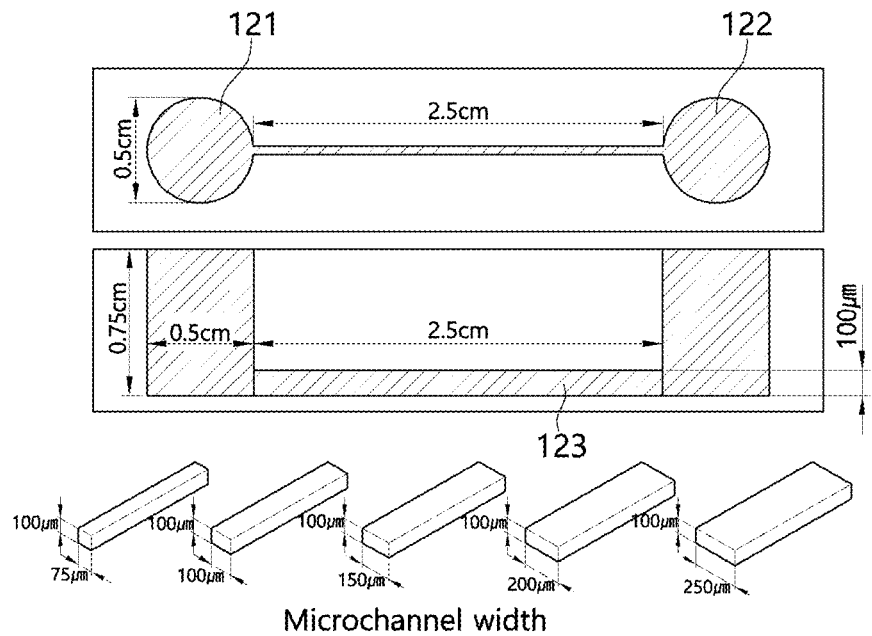
FIG. 5(A) shows an example of an experiment for determining the width of a channel that connects the first chamber to the second chamber.
Figure 5B:
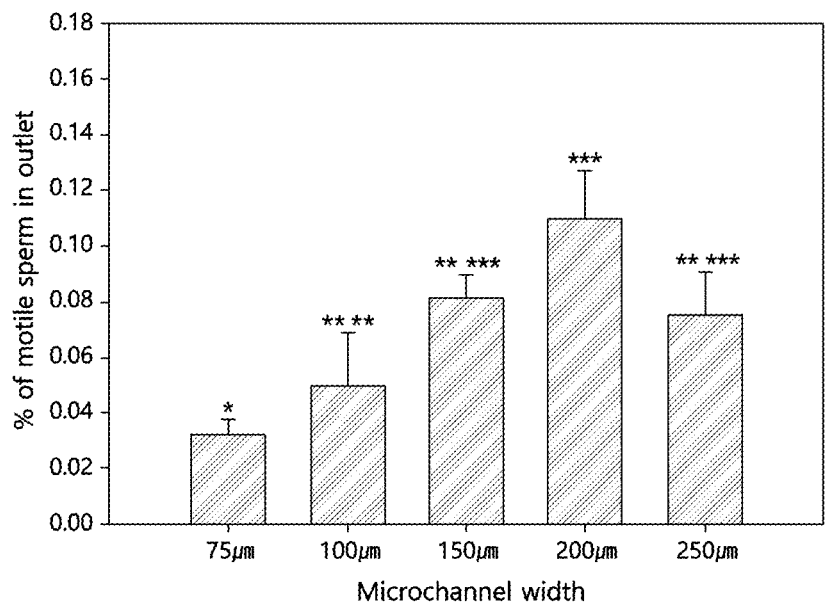
FIG. 5(B) shows a result of an experiment for observing the percentage of sperms that moved to the opposite chamber using the channel of FIG. 5(A).

FIG. 5 shows an example of an experimental for determining a microchannel width efficient for sperm movement. As shown therein, microchips having a microchannel height of 100 μm, a microchannel length of 2.5 cm and microchannel widths of 75, 100, 150, 200 and 250 μm, respectively, were fabricated and used in the experiment (FIG. 5(a)).

M16 medium was filled into each of the fabricated microchips, and $5 \times 10^5$ motile sperms, selected by the swim-up method and added to 10 μl of M16 medium, were loaded slowly into the left chamber. Each of the microchips was incubator in an incubator at 37° C. in a 5% $CO_2$ atmosphere for 90 minutes, and the percentage of sperms that moved to the opposite chamber was measured. As a result, the significantly highest percentage of sperms that moved to the opposite chamber was observed in the microchip having a microchannel width of 200 μm (FIG. 5(b)).

Data shown are mean±SD of values obtained through three independent experiments (p<0.05).

Figure 6A:
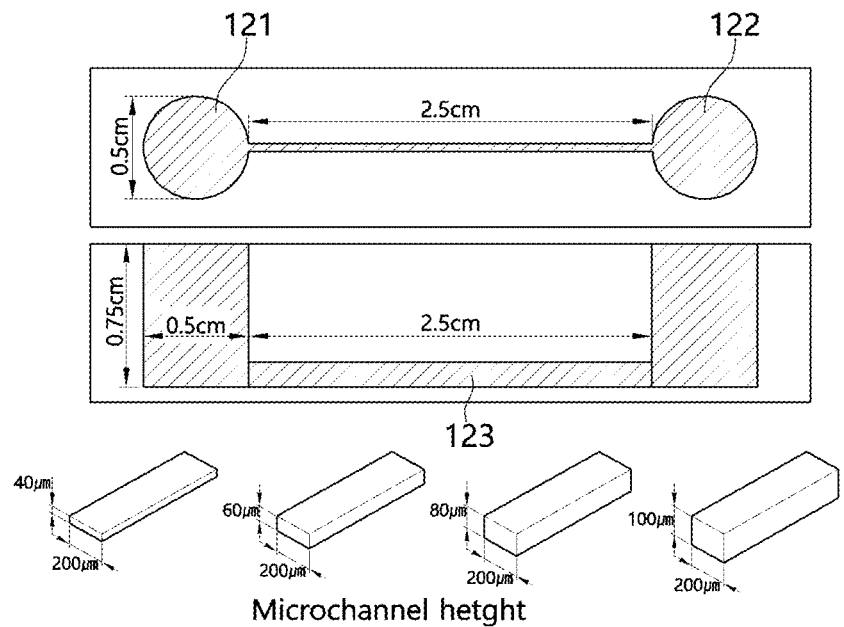
FIG. 6(A) shows an example of an experiment for determining the height of a channel that connects the first chamber to the second chamber.
Figure 6B:
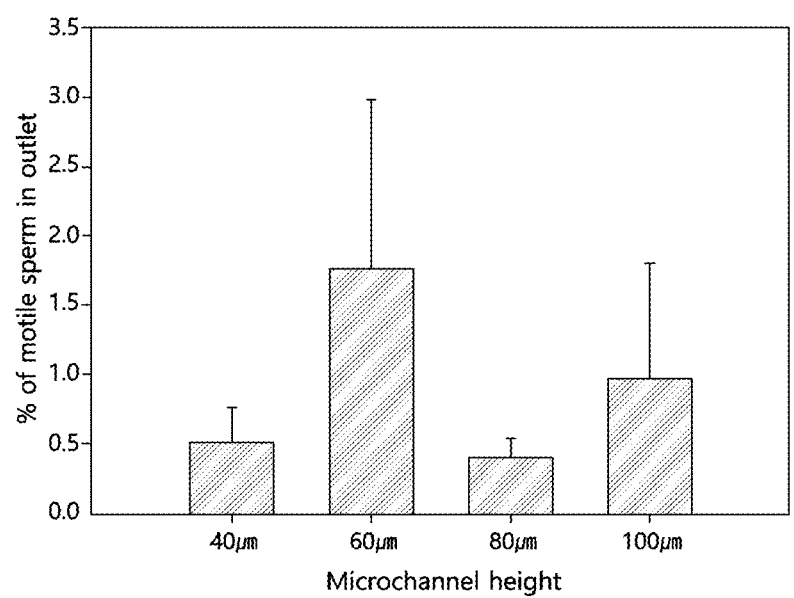
FIG. 6(B) shows a result of an experiment for observing the percentage of sperms that moved to the opposite chamber using the channel of FIG. 6(A).

FIG. 6 shows an example of an experiment for determining a microchannel height efficient for sperm movement. As shown therein, microchips having a microchannel width of 200 μm, a microchannel length of 2.5 cm and microchannel heights of 40, 60, 80 and 100 μm, respectively, were fabricated and used in the experiment (FIG. 6(a)).

M16 medium was filled into each of the fabricated microchips, and $5 \times 10^5$ motile sperms, selected by the swim-up method and added to 10 μl of M16 medium, were loaded slowly into the left chamber. Each of the microchips was incubator in an incubator at 37° C. in a 5% $CO_2$ atmosphere for 90 minutes, and the percentage of sperms that moved to the opposite chamber was measured. As a result, the significantly highest percentage of sperms that moved to the opposite chamber was observed in the microchip having a microchannel height of 60 μm (FIG. 6(b)).

Data shown are mean±SD of values obtained through three independent experiments.

Figure 7A:
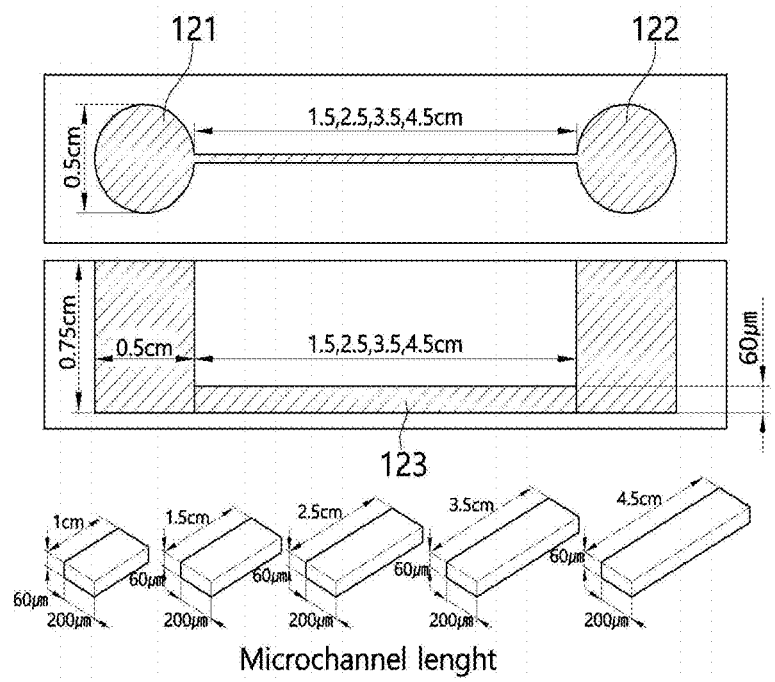
FIG. 7(A) shows an example of an experiment for determining the length of a channel that connects the first chamber to the second chamber.
Figure 7B:
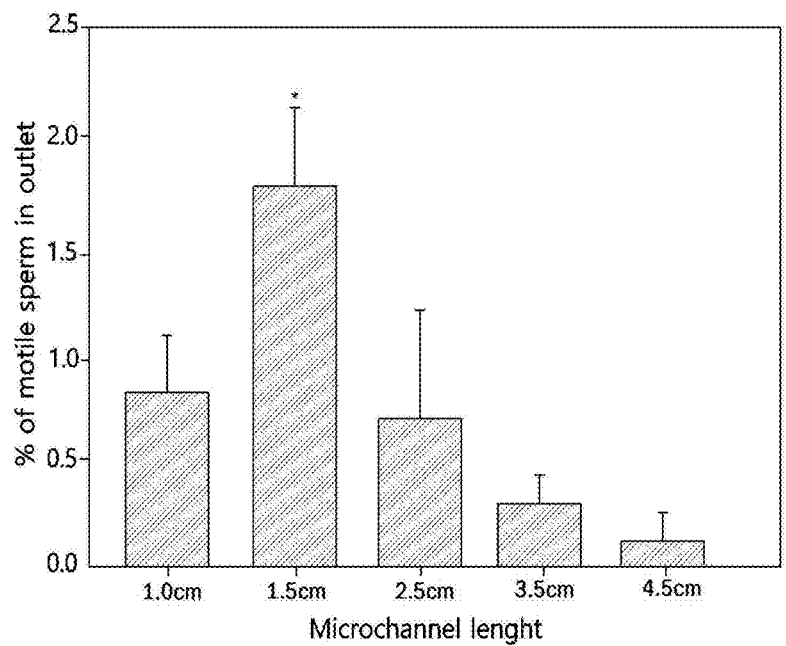
FIG. 7(B) shows a result of an experiment for observing the percentage of sperms that moved to the opposite chamber using the channel of FIG. 7(A).

FIG. 7 shows an experimental example for determining a microchannel length efficient for sperm movement. As shown therein, microchips having a microchannel width of 200 μm, a microchannel height of 60 μm and microchannel lengths of 1.0, 1.5, 2.5, 3.5 and 4.5 cm, respectively, were fabricated and used in the experiment (FIG. 7(a)).

M16 medium was filled into each of the fabricated microchips, and $5 \times 10^5$ motile sperms, selected by the swim-up method and added to 10 μl of M16 medium, were loaded slowly into the left chamber. Each of the microchips was incubated in an incubator at 37° C. in a 5% $CO_2$ atmosphere for 90 minutes, and the percentage of sperms that moved to the opposite chamber was measured. As a result, the significantly highest percentage of sperms that moved to the opposite chamber was observed in the microchip having a microchannel length of 1.5 cm (FIG. 7(b)).

Data shown are mean±SD of values obtained through three independent experiments (p<0.05).

Based on these results, it could finally be concluded that the structural conditions of the microchannel, through which sperms can easily move to the fallopian tube, are a width of 200 μm, a height of 60 μm, and a length of 1.5 cm.

2.2. Analysis of the Efficiency with Which Capacitated Motile Sperms are Produced in Microchip Mimicking Female Reproductive Organs In order to examine whether only capacitated motile sperms can be selectively retrieved after sperm capacitation in the optimized microchip mimicking female reproductive organs was achieved, sperm capacitation in each of a conventional plastic culture dish (control) and the microchip was induced. Next, the percentages of dead sperms after capacitation induction, immotile live sperms after capacitation induction, live motile sperms after capacitation induction and live motile capacitated sperms after capacitation induction in the capacitation-induced sperm population were measured.

Table 1 below shows the results of analyzing the state of sperms after capacitation induction in each of the conventional plastic culture dish and the microchip optimized for sperm movement.

TABLE 1

| Type of dish for sperm capacitation | %$^a$ of dead sperms after capacitation induction | %$^a$ of live immotile sperms after capacitation induction | %$^a$ of live motile sperms after capacitation induction | %$^b$ of live motile capacitated sperms after capacitation induction |
|---|---|---|---|---|
| Conventional plastic culture dish | 4.7$^c$ | 77.5$^c$ | 17.8$^c$ | 10.0$^c$ |
| PDMS-based microchip | 0$^d$ | 0$^d$ | 100$^d$ | 52.5$^d$ |

Model effects of treatments in each parameter, as indicated by p values, were 0.0130, <0.0001, 0.0002 and <0.0001 in dead sperms after capacitation induction, immotile sperms after capacitation induction, motile sperms after capacitation induction, and motile capacitated sperms after capacitation induction, respectively.

$^a$ Percentage relative to the total number of recovered sperms after capacitation induction.

$^b$ Percentage relative to the total number of live motile sperms after capacitation induction.

$^{c,\,d}$ p<0.05.

As shown in Table 1 above, after capacitation of ejaculated sperms was induced under each condition, the efficiency with which live motile sperms and live motile capacitated sperms were produced in the microchip was significantly higher than that in the conventional plastic culture dish (control).

However, the efficiency with which dead sperms after capacitation induction and live immotile sperms after capacitation induction were produced in the conventional plastic culture dish was significantly higher than that in the microchip.

From these results, it was found that the microchip 100 mimicking female reproductive organs could effectively produce motile capacitated good-quality sperms from sperms ejaculated outside the body.

2.3. Analysis of the Efficiency of In Vitro Fertilized Embryo Production in Microchip Mimicking Female Reproductive Organs and the In Vitro Developmental Rate of In Vitro Fertilized Embryos In vitro fertilization of mature oocytes with the capacitated mature sperms that moved from the vagina-corresponding space of the optimized microchip mimicking female reproductive organs to the fallopian tube-corresponding space was performed, and the efficiency of production of in vitro fertilized embryos in the in vitro fertilization was measured.

Table 2 below compares the efficiency of production of in vitro fertilized embryos with that in the optimized microchip for recovery of capacitated sperms.

TABLE 2

| Type of dish for in vitro fertilization | Number of mature oocytes$^a$ used for in vitro fertilization | Number [%]$^c$ of in vitro fertilized embryos$^b$ produced |
|---|---|---|
| Conventional plastic culture dish | 70 | 60 [85.7] |
| PDMS-based microchip | 57 | 49 [86.0] |

TABLE 2-continued

| Type of dish for in vitro fertilization | Number of mature oocytes$^a$ used for in vitro fertilization | Number [%]$^c$ of in vitro fertilized embryos$^b$ produced |
|---|---|---|

Model effects of treatments in each parameter, expressed as p value, were 0.9682 in the efficiency of in vitro fertilized embryos.
$^a$MII-stage mature oocytes having a first polar body and cumulus cells were collected 16 hours after hCG injection.
$^b$1-Cell embryos having a pronucleus and a second polar body were collected after mature oocytes collected 16 hours after hCG injection were incubated with sperms for 6 hours.
$^c$Percentage relative to the number of mature oocytes used for in vitro fertilization.

As shown in Table 2 above, the efficiency of production of in vitro fertilized embryos in the microchip did not significantly differ from that in the conventional plastic culture dish (control).

However, when the 1-cell-stage in vitro fertilized embryos produced in the conventional plastic culture dish and the microchip were cultured under the same in vitro conditions, the in vitro fertilized embryos produced in the microchip showed a significantly higher in vitro developmental rate of 4-cell embryos and blastocysts compared to the in vitro fertilized embryos produced in the conventional plastic culture dish.

Table 3 below compares the in vitro developmental rate of the in vitro fertilized embryos produced in the conventional plastic culture dish with that in the optimized microchip for retrieval of capacitated mature sperms.

TABLE 3

| Type of fish for in vitro fertilization | Number of in vitro fertilized embryos$^a$ cultured | Number (%)$^b$ of embryos developed to | | |
|---|---|---|---|---|
| | | 2-cell [48]$^c$ | 4-cell [72]$^c$ | Blastocyst [144]$^c$ |
| Conventional plastic culture dish | 41 | 41 [100] | 28 [69.3]$^d$ | 0 [0]$^d$ |
| PDMS-based microchip | 41 | 41 [100] | 33 [80.5]$^e$ | 30 [73.1]$^e$ |

Model effects of treatments in each parameter, as indicated by p values, were 1.0000, 0.2107 and <0.0001 in the development to the 2-cell stage, 4-cell stage and blastocyst stage, respectively.
$^a$1-Cell embryos having a pronucleus and a second polar body were collected after mature oocytes collected 16 hours after hCG injection were incubated with sperms for 6 hours.
$^b$Percentage relative to the number of in vitro fertilized embryos cultured.
$^c$Numbers in parentheses indicate time after hCG injection.

In vitro fertilized embryos were placed in a culture dish made of silicone, and were then cultured in BSA-free M16 medium from the onset of culture, and BSA (3 mg/ml) was added to the M16 medium from 72 hours after hCG injection.

$^{d,\,e}$ Different subscripts within the same column are significantly different (p<0.05).

These results indicate that the optimized microchip mimicking female reproductive organs has no significant effect on the efficiency of production of in vitro fertilized embryos, but makes it possible to produce good-quality in vitro fertilized embryos by producing good-quality capacitated motile sperms.

In addition, the optimized microchip mimicking female reproductive organs may be used as an effective tool that enables uncapacitated sperms to be self-capacitated and makes it possible to produce good-quality in vitro fertilized embryos by meeting these sperms to meet mature oocytes. This microchip can be of great help in producing good-quality in vitro fertilized embryos in the future breeding-related industry.

As described above, to solve infertility problems based on improvement in the efficiency of assisted reproductive technologies, it is very important to produce good-quality in vitro fertilized embryos, and a technology capable of easily selecting good-quality capacitated motile sperms from semen and a technology capable of effectively producing embryos by causing these sperms to meet mature oocytes are urgently required.

The microchip according to the present invention structurally mimics in vivo organs, including vagina, cervix, uterus, isthmus, and fallopian tube, which produce embryos by selecting capacitated motile sperms from semen and causing the selected sperms to meet mature oocytes. Thus, the microchip is capable of effectively producing motile capacitated good-quality sperms from sperms ejaculated outside the body.

The microchip according to the present invention may be used as an effective tool that enables uncapacitated sperms to be self-capacitated and makes it possible to produce good-quality in vitro fertilized embryos by meeting these sperms to meet mature oocytes.

Therefore, the microchip according to the present invention can be of great help in producing good-quality in vitro fertilized embryos in the future breeding-related industry.

The above description of the present invention is exemplary, and those of ordinary skill in the art will appreciate that the present invention can be easily modified into other specific forms without departing from the technical spirit or essential characteristics of the present invention.

Therefore, it should be understood that the exemplary embodiments described above are exemplary in all aspects and are not restrictive. For example, each component described to be of a single type can be implemented in a distributed manner. Likewise, components described to be distributed can be implemented in a combined manner.

The scope of the present invention is defined by the following claims rather than by the detailed description of the invention. It shall be understood that all modifications and embodiments conceived from the meaning and scope of the claims and their equivalents are included in the scope of the inventive concept.

What is claimed is:

1. A microchip mimicking female reproductive organs for capacitated motile sperms, the microchip comprising:
   a first chamber formed in a predetermined member and having a predetermined depth;
   a second chamber formed in the member and having a predetermined depth; and
   a channel connected to a bottom of each of the first chamber and the second chamber and connecting the first chamber to the second chamber,
   wherein the member comprises polydimethylsiloxane (PDMS),
   wherein the first chamber and the second chamber, which have a cylindrical shape, have a diameter of 0.5 cm,
   wherein the channel connecting the first chamber to the second chamber has a rectangular tube shape with a straight line shape,
   wherein the channel has a length of 1.5 cm, a width of 200 µm, and a height of 60 µm.

2. A method for producing capacitated motile sperms, the method comprising the steps of:
   injecting sperms into the first chamber of the microchip mimicking female reproductive organs set forth in claim 1;
   incubating the microchip for a predetermined time; and
   selecting sperms that moved to the second chamber through the channel.

\* \* \* \* \*